United States Patent
Bailey et al.

(10) Patent No.: US 10,656,131 B1
(45) Date of Patent: May 19, 2020

(54) CAVITY ENHANCED ABSORPTION SPECTROSCOPY (CEAS) FOR OZONE DETECTION

(71) Applicant: United States of America as represented by the Administrator of NASA, Washington, DC (US)

(72) Inventors: Steven A. Bailey, Gambrills, MD (US); Thomas Hanisco, Takoma Park, MD (US)

(73) Assignee: United States of America as represented by the Administrator of NASA, Washington, DC (US)

(*) Notice: Subject to any disclaimer, the term of this patent is extended or adjusted under 35 U.S.C. 154(b) by 0 days.

(21) Appl. No.: 16/109,093

(22) Filed: Aug. 22, 2018

(51) Int. Cl.
  *G01N 21/00* (2006.01)
  *G01N 33/00* (2006.01)
  *G01N 21/17* (2006.01)

(52) U.S. Cl.
  CPC ..... *G01N 33/0039* (2013.01); *G01N 21/1702* (2013.01); *G01N 2021/1704* (2013.01)

(58) Field of Classification Search
  CPC .. G01N 21/39; G01N 21/3504; G01N 21/031; G01N 2021/399; G01J 3/42
  USPC .......... 356/437
  See application file for complete search history.

(56) References Cited

U.S. PATENT DOCUMENTS

| | | | |
|---|---|---|---|
| 7,301,639 B1* | 11/2007 | Kebabian | G01N 21/031 356/437 |
| 2012/0001083 A1* | 1/2012 | Knapp | G01J 3/02 250/370.12 |
| 2017/0219479 A1* | 8/2017 | Bilenko | G01N 21/031 |
| 2018/0265385 A1* | 9/2018 | Yamauchi | C02F 9/00 |
| 2019/0226987 A1* | 7/2019 | Birks | G01N 15/06 |

* cited by examiner

*Primary Examiner* — Md M Rahman
(74) *Attorney, Agent, or Firm* — Christopher O. Edwards; Bryan A. Geurts

(57) ABSTRACT

Cavity enhanced absorption spectroscopy (CEAS) may include a pulsed light emitting diode (LED) configured to emit a light towards a photomultiplier tube (PMT). CEAS may also include a cell, which includes a pair of reflective mirrors located at opposite ends of the cell. The pair of mirrors are configured to bounce the light back and forth a plurality of times increasing the effective path length of the cell. The PMT is configured to detect the emitted light for ozone absorption measurement.

16 Claims, 3 Drawing Sheets

300

CAVITY ENHANCED ABSORPTION SPECTROSCOPY (CEAS) FOR OZONE DETECTION

STATEMENT OF FEDERAL RIGHTS

The invention described herein was made by employees of the United States Government and may be manufactured and used by or for the Government for Government purposes without the payment of any royalties thereon or therefore.

FIELD

The present invention relates to measuring absorption of ozone, and more particularly, to cavity enhanced absorption spectroscopy (CEAS) configured to measure absorption of ozone.

BACKGROUND

Ozone is an important atmospheric pollutant and greenhouse gas. Improved sensitivity is required to make faster sampling of ozone at high precision. Existing optical instrumentation does not have precision to sample low concentration at fast time resolution (e.g., faster than once per second). More specifically, because the aircraft moves approximately 200 meters per second, the integration time cannot be 10 s of seconds; otherwise, fine spatial resolution will not be achieved.

Thus, an alternative approach for measuring absorption of ozone may be beneficial.

SUMMARY

Certain embodiments of the present invention may provide solutions to the problems and needs in the art that have not yet been fully identified, appreciated, or solved by current ozone detection instrumentations. For example, some embodiments generally pertain to CEAS configured to measure absorption of ozone quickly and with high precision.

In an embodiment, an apparatus may include a pulsed light emitting diode (LED) configured to emit light towards a photomultiplier tube (PMT). The apparatus may also include a cell, which includes a pair of reflective mirrors located at opposite ends of the cell. The pair of mirrors are configured to bounce the light back and forth a plurality of times increasing the effective path length of the cell. The PMT is configured to detect the emitted light for ozone absorption measurement.

In another embodiment, an apparatus includes a PMT configured to detect light emitted by a pulsed LED for ozone absorption measurement. The apparatus also includes a cell placed between the pulsed LED and the PMT, configured to extend the optical path for the light. The cell includes a pair of reflective mirrors located at opposite ends of the cell. The pair of mirrors are configured to bounce the light back and forth a plurality of times increasing the effective path length of the cell.

In yet another embodiment, an apparatus includes a cell placed between a PMT and a pulsed LED. The cell includes a pair of mirrors configured to extend the optical path of the cell, such that the optical path is significantly greater than the physical path of the cell. The PMT is configured to detect light emitted by the LED for ozone absorption measurement.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE EMBODIMENTS

Ozone is a greenhouse gas and pollutant that absorbs strongly at specific wavelengths in the ultraviolet (UV). To measure absorption of ozone, some embodiments generally pertain to CEAS. CEAS may measure absorption quickly and with high precision.

In an embodiment, CEAS may project UV light through a cell bounded by highly reflective mirrors. UV light, which enters the cell, may bounce back and forth many times increasing the effective path length of the cell. This increased path length increases the chance of ozone absorption within the cell. The absorption measurement is made using a detector located outside of the cell and opposite to the UV light source.

In some embodiments, CEAS improves precision for the detection of ozone of 0.12 parts per billion (ppb) in 0.1 second integration. This corresponds to 0.012 ppb in ten seconds integration. This also compares with a typical, commercially available optical based ozone instrument that has a precision of 1.5 ppb in ten seconds integration.

The combination of CEAS with a simple and inexpensive optical and electrical design to achieve a high quality of ozone measurement is superior to that of commercial optical instruments. The sensitivity of this approach exceeds that of commercial optical instruments and matches that of highly complex chemiluminescence instruments. Chemiluminescence instruments are complex, difficult to transport (e.g., they require dry ice and compressed nitric oxide), and therefore, are difficult to maintain on an aircraft. Unlike complex chemiluminescence instruments, CEAS is simple, compact, and easy to maintain on an aircraft.

Figure 1:
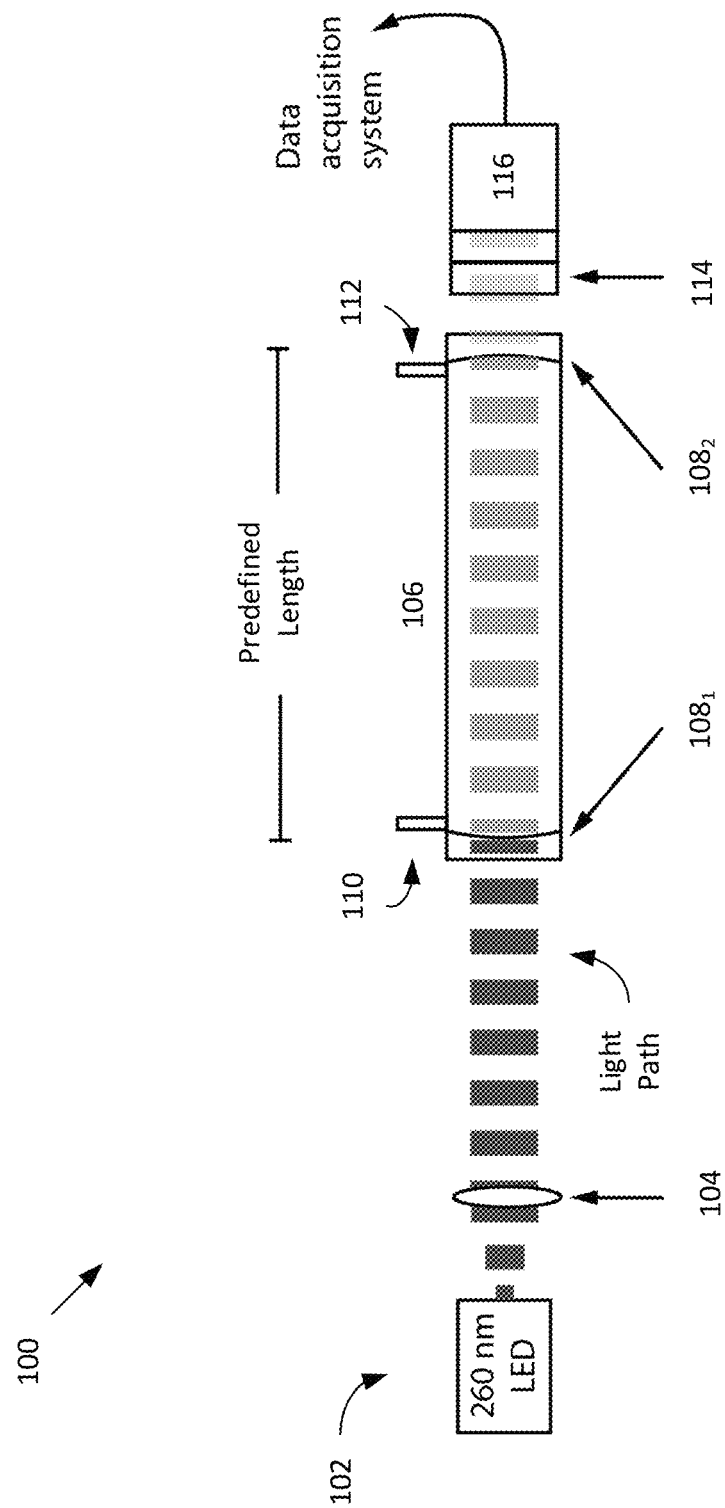
FIG. 1 is a diagram illustrating CEAS for measuring absorption of ozone, according to an embodiment of the present invention.

FIG. 1 is a diagram illustrating CEAS 100 for measuring absorption of ozone, according to an embodiment of the present invention. In some embodiments, CEAS 100 includes a gas sample cell (hereinafter "cell") 106 having a predefined length. The predefined length in some embodiments is determined by ozone sensitivity required for the application. For example, the longer the cell, the more sensitive. Likewise, shorter the cell, the less sensitive. In some embodiments, the cell length is selected by the maximum length that fits into an aircraft rack.

Also, in this embodiment, cell 106 may include two highly reflectively mirrors $108_1$ and $108_2$. Mirrors $108_1$, $108_2$ are 99.999 percent reflective and curved in some embodiments. The curvature (radius) of mirrors $108_1$, $108_2$ may be within the length of cell 106 (plus or minus 50 percent). The high reflectivity of mirror $108_1$ allows light to be leaked in by the cavity formed within mirror $108_1$. The leaked light may bounce back and forth for at least hundreds of passes before the light is leaked out by way of mirror $108_2$. One would appreciate that mirrors $108_1$ and $108_2$, which are highly reflective, create a longer optical path than what is provided by the physical path within cell 106. This allows for a path length (e.g., of 50 or 100 meters) to be easily achieved.

The optical path length is dependent on the physical path length within cell 106. In other words, with the longer the physical path length, a longer optical path length is realized. Furthermore, although FIG. 1 illustrates two mirrors $108_1$, $108_2$, the number of mirrors may increase depending on the configuration of CEAS.

Conventional ozone detection instruments may use lasers and alignment mechanisms for aligning the mirrors. In these embodiments, however, a LED source 102 is utilized. For example, LED source 102 may emit light towards cell 106. The intensity of the light may depend on the requirement of the mission.

Because light may scatter in all directions, a coupling lens 104 is placed between LED source 102 and cell 106. Coupling lens 104 may increase the light moving towards cell 106. As discussed above, as light enters cell 106, the light leaks through a cavity of mirror $108_1$ and bounces back and forth hundreds of times. This essentially extends the path length of the light.

Simultaneously, gas enters into cell 106 by way of inlet 110 and out from cell 106 by way of outlet 112. The light and the gas may mix while the light is bouncing back and forth within cell 106. A small amount of light may exit (or leak) through mirror $108_2$. This light may be detected by a photomultiplier tube (or PMT) 116.

PMT 116 may convert the detected photons into an electrical signal. For example, with a pulsed LED light, the light is measured when LED source 102 emits a light towards PMT 116 and the background of PMT 116 is subtracted when LED source 102 is off. In other words, the difference between LED source 102 being on and LED source being off is always being measured. This greatly improves the signal to noise.

In some embodiments, ozone is measured by introducing the gas into cell 106 and measuring the attenuation of the light in the PMT signal. The wavelength of the light is important in some embodiments. For example, the light may be emitted by LED source 102 operating at 260 nanometers, which is near the peak absorption of ozone.

Also, in some embodiments, prior to the light being detected by PMT 116, a series of optical bandpass filters 114, which are placed in front of PMT 116, may filter one or more sources of light that are otherwise not associated with LED source 102. For example, room light, which contributes noise to the measurement of ozone, is blocked by the series of optical bandpass filters 114. Additionally, optical bandpass filters 114 may narrow down the wavelength region of the light to ensure that the light detected by PMT 116 has made at least a hundred passes or so through cell 106.

Ozone concentration is determined from Beer's law, which described the attenuation of light by an absorber per unit length $$I/I_0 = e^{-\sigma n l} \quad \text{Equation (1)}$$

where I is measured light intensity with the absorber ($O_3$) in cell 106, $I_0$ is measured light with no absorber ($O_3$) in cell 106, a is the absorption cross section of ozone at 260 nm, n is the number of $O_3$ molecules in cell 106, and l is the optical path length of cell 106.

Figure 2:
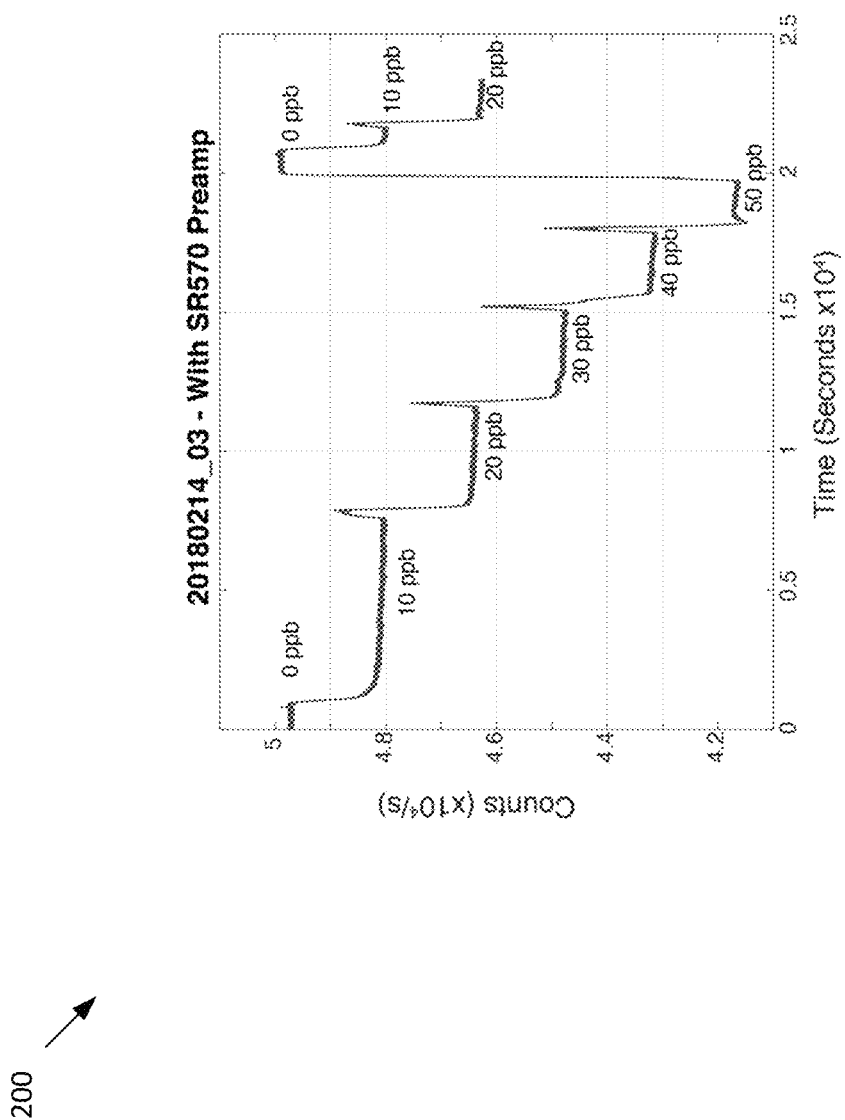
FIG. 2 is a graph illustrating measurement of transmission intensity through the $O_3$ absorption cell, according to an embodiment of the present invention.
Figure 3:
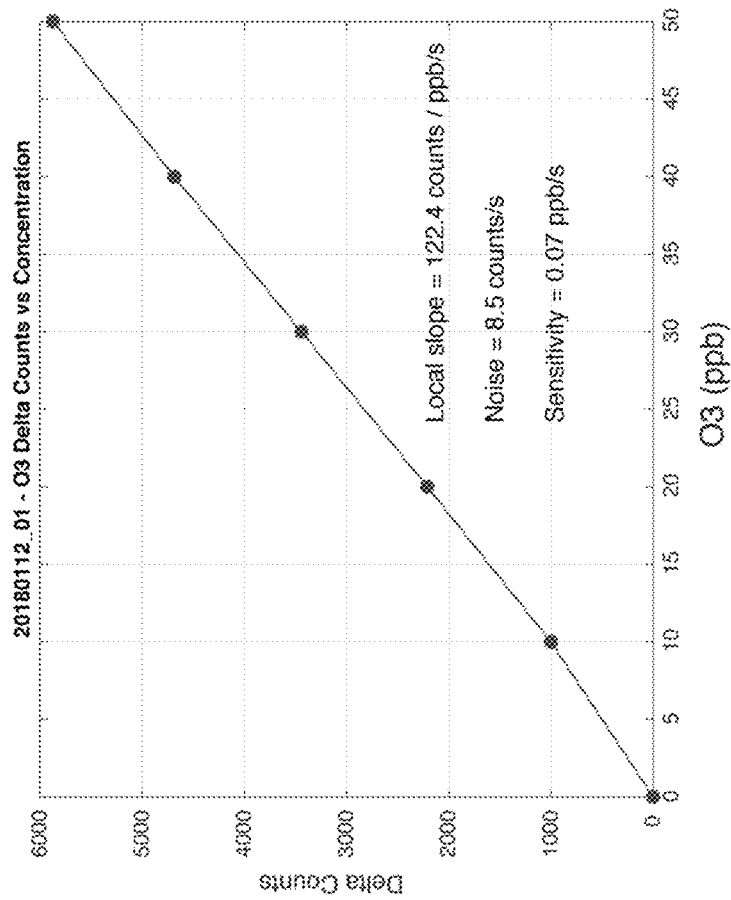
FIG. 3 is a graph illustrating sensitivity of CEAS instrument, according to an embodiment of the present invention.

This equations defines the measurements shown in graph 200 of FIG. 2 and graph 300 of FIG. 3. FIG. 2 is a graph 200 illustrating measurement of transmission intensity through the $O_3$ absorption cell, according to an embodiment of the present invention. In graph 200, with no ozone in the cell, 0 parts per billion (ppb) is equivalent to $I_0$. When ozone is introduced within the cell, the signal decreases because ozone is absorbing light within the cell. Graph 200 also shows that with ozone concentration being increased, lower and lower transmission is realized in the cell. This shows the precision of CEAS instrument.

FIG. 3 is a graph 300 illustrating sensitivity of CEAS instrument, according to an embodiment of the present invention. Graph 300 shows the sensitivity versus concentration, e.g., as the concentration (or ppb) increases, the delta counts or sensitivity increases.

In some embodiments, CEAS may include a pulsed LED configured to emit a light towards a PMT. CEAS may also include a cell, which includes a pair of reflective mirrors located at opposite ends of the cell. The pair of mirrors are configured to bounce the light back and forth a plurality of times increasing the effective path length of the cell. The PMT is configured to detect the emitted light for ozone absorption measurement.

It will be readily understood that the components of various embodiments of the present invention, as generally described and illustrated in the figures herein, may be arranged and designed in a wide variety of different configurations. Thus, the detailed description of the embodiments, as represented in the attached figures, is not intended to limit the scope of the invention as claimed but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. An apparatus, comprising:
a pulsed light emitting diode (LED) configured to emit a light operating at a 260 nanometer wavelength towards a photomultiplier tube (PMT); and
a cell comprising a pair of reflective mirrors located at opposite ends of the cell, wherein the pair of mirrors are configured to bounce the light back and forth a plurality of times increasing the effective path length of the cell, wherein the PMT is configured to detect the emitted light for ozone absorption measurement with a shortened integration time of a duration of less than 10 seconds made from an aircraft moving approximately 200 meters per second in order to achieve a predetermined fine spatial resolution of 0.12 parts per billion where the duration is approximately 0.1 seconds; whereby the attenuation of light by an absorber per unit length is defined by the equation $I/I_0=e^{-\sigma nl}$, where I is measured light intensity with the absorber ($O_3$) in a cell, $I_0$ is measured light with no absorber ($O_3$) in the cell, $\sigma$ is the absorption cross section of ozone at 260 nm, n is the number of $O_3$ molecules in the cell, and l is the optical path length of the cell.

2. The apparatus of claim 1, wherein the cell has a predefined length determined by ozone sensitivity required for an application.

3. The apparatus of claim 1, wherein one of the pair of mirrors is configured to allow light emitted from the pulsed LED into the cell.

4. The apparatus of claim 1, wherein another one of the pair of mirrors is configured to allow the light to leak out of the cell and towards the PMT.

5. The apparatus of claim 1, further comprising:
a coupling lens placed between the pulsed LED and the cell, configured to increase an intensity of the light moving towards the cell.

6. The apparatus of claim 1, wherein the cell comprises an inlet configured to introduce gas to flow into the cell and mix with the light.

7. The apparatus of claim 1, further comprising:
a series of optical bandpass filters in front of the PMT, configured to filter one or more sources of light not associated with the LED source.

8. The apparatus of claim 7, wherein the series of optical bandpass filters are further configured to narrow down a wavelength region of the light to ensure that the light detected by the PMT made at least a hundred passes through the cell.

9. An apparatus, comprising:
a photomultiplier tube (PMT) configured to detect light emitted by a pulsed light emitting diode (LED) operating at a 260 nanometer wavelength for ozone absorption measurement; and
a cell placed between the pulsed LED and the PMT, configured to extend the optical path for the light, wherein
the cell comprises a pair of reflective mirrors located at opposite ends of the cell, the pair of mirrors are configured to bounce the light back and forth a plurality of times increasing the effective path length of the cell; wherein the PMT is configured to detect the emitted light for ozone absorption measurement with a shortened integration time of a duration of less than 10 seconds made from an aircraft moving approximately 200 meters per second in order to achieve a predetermined fine spatial resolution of 0.12 parts per billion where the duration is approximately 0.1 seconds; whereby the attenuation of light by an absorber per unit length is defined by the equation $I/I_0=e^{-\sigma nl}$, where I is measured light intensity with the absorber ($O_3$) in a cell, $I_0$ is measured light with no absorber ($O_3$) in the cell, $\sigma$ is the absorption cross section of ozone at 260 nm, n is the number of $O_3$ molecules in the cell, and l is the optical path length of the cell.

10. The apparatus of claim 9, wherein the cell has a predefined length determined by ozone sensitivity required for an application.

11. The apparatus of claim 9, wherein one of the pair of mirrors is configured to allow light emitted from the pulsed LED into the cell.

12. The apparatus of claim 9, wherein another one of the pair of mirrors is configured to allow the light to leak out of the cell and towards the PMT.

13. The apparatus of claim 9 further comprising:
a coupling lens placed between the pulsed LED and the cell, configured to increase an intensity of the light moving towards the cell.

14. The apparatus of claim 9, wherein the cell comprises an inlet configured to introduce gas to flow into the cell and mix with the light.

15. The apparatus of claim 9, further comprising:
a series of optical bandpass filters in front of the PMT, configured to filter one or more sources of light not associated with the LED source.

16. The apparatus of claim 15, wherein the series of optical bandpass filters are further configured to narrow down a wavelength region of the light to ensure that the light detected by the PMT made at least a hundred passes through the cell.

* * * * *